United States Patent [19]

Kadin

[11] 4,321,372

[45] Mar. 23, 1982

[54] ANTIULCER THIAZOL-2-YLCARBAMOYL-CARBOXYLIC ACIDS, ESTERS AND AMIDES

[75] Inventor: Saul B. Kadin, New London, Conn.

[73] Assignee: Pfizer Inc., New York, N.Y.

[21] Appl. No.: 160,046

[22] Filed: Jun. 16, 1980

[51] Int. Cl.³ .......................................... C07D 277/20
[52] U.S. Cl. .................................. 544/133; 548/195;
424/270; 546/198; 546/209; 424/248.51;
424/267
[58] Field of Search ....................... 548/195, 200, 190;
546/209, 198; 424/270; 544/133

[56] References Cited

U.S. PATENT DOCUMENTS

| | | | |
|---|---|---|---|
| 3,966,965 | 6/1976 | Sellstedt et al. ................ | 424/309 |
| 4,150,140 | 2/1976 | Hall et al. ....................... | 424/270 |
| 4,182,766 | 1/1980 | Krasso ............................ | 426/270 |
| 4,183,854 | 1/1980 | Crossley ......................... | 548/195 |
| 4,238,496 | 12/1980 | Hess et al. ...................... | 548/195 |
| 4,246,271 | 1/1981 | Cousse et al. ................... | 548/195 |

FOREIGN PATENT DOCUMENTS

| | | |
|---|---|---|
| 6368 | 1/1980 | European Pat. Off. . |
| 1538822 | 1/1979 | United Kingdom . |
| 2023580 | 1/1980 | United Kingdom . |

OTHER PUBLICATIONS

Sellstedt et al.; J. Med. Chem. 1869, pp. 926-933 (1975).

Primary Examiner—Nicholas S. Rizzo

Attorney, Agent, or Firm—Charles J. Knuth; Albert E. Frost; Peter C. Richardson

[57] ABSTRACT

This invention encompasses orally effective antiulcer agents of the formula

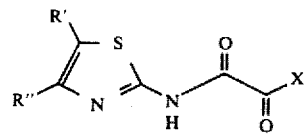

wherein
  X is hydroxy, $(C_1-C_5)$-alkoxy, phenoxy, benzyloxy, or —$NH(CH_2)_nY$ wherein n is an integer of value 2 to 4 and Y is di-$(C_1-C_3)$-alkylamino, 1-pyrrolidinyl, 1-piperidinyl or 4-morpholinyl;
  R' and R" when taken together are $(C_3-C_8)$-alkylene, with the proviso that the ring so formed is 5- to 8-membered;
  R' and R" when taken separately are each independently hydrogen, $(C_1-C_6)$-alkyl or $(C_5-C_6)$-cycloalkyl, with the proviso that when X is other than —$NH(CH_2)_nY$, at least one of R' and R" is other than hydrogen;
  the pharmaceutically acceptable cationic salts thereof when X is hydroxyl, and the pharmaceutically acceptable anionic salts thereof when X is —$NH(CH_2)_nY$.

22 Claims, No Drawings

ANTIULCER THIAZOL-2-YLCARBAMOYL-CARBOXYLIC ACIDS, ESTERS AND AMIDES

BACKGROUND OF THE INVENTION

This invention relates to novel thiazol-2-ylcarbamoylcarboxylic acids, esters and amides having utility in the prevention and treatment of peptic ulcers, particularly gastric ulcers.

A peptic ulcer is defined as circumscribed ulceration of the mucous membrane penetrating through the muscularis mucosa and occurring in areas bathed by acid and pepsin. Peptic ulcers most commonly are found along the lesser curvature of the stomach (gastric ulcers) and in the first few centimeters of the duodenum, known as the duodenal bulb (duodenal ulcers).

There is but limited understanding of the cause of peptic ulcers. While it is known that peptic ulcers are absent if the stomach does not secrete acid, nearly all humans secrete acid, so that it remains to be established why some develop ulcers and others do not. There appears to be a balance between ulcer-promoting factors, such as the excessive secretion of acid or pepsin, and the mucosal protective factors, such as mucus production, membrane barriers to permeability, or mucosal cell turnover time. This balance can be disturbed at a number of points and by many factors. Stress has been implicated as a commonly occurring precipitating factor, as has the administration of certain drugs, such as corticosteroids, phenylbutazone, and reserpine.

A variety of treatments for peptic ulcers have been developed. The treatment depends upon the severity of the ulcer and may range from dietary and medical (drug) treatment to surgery.

Treatment of gastric and duodenal ulcer is frequently designed to neutralize or decrease gastric acidity even though gastric acidity is usually normal in patients with gastric ulcer. Although there is no proof that antacids promote healing or prevent recurrence, there is general agreement that they give symptomatic relief. Antacids such as sodium bicarbonate and calcium carbonate are the most potent antacids, but they are absorbable and continuous use is prone to cause alkalosis or the so-called milk alkali syndrome. Symptoms are not distinctive and these complications can progress unrecognized to irreversible kidney damage. Aluminum hydroxide, which is nonabsorbable, is also commonly used as an antacid. However, phosphate depletion can occur from gastrointestinal binding of phosphate by aluminum—causing phosphorous blood levels to decrease and phosphorous resorption from bone to increase, reflected in weakness, malaise and anorexia. Bone demineralization can ultimately occur, if the diet does not provide adequate phosphorus. Aluminum hydroxide also causes constipation, and so is usually combined with magnesium hydroxide, also a nonabsorbable antacid, but also a cathartic. Even on low daily doses, patients can require careful titration to avoid one or the other of the aluminum/magnesium hydroxide side-effects of constipation or diarrhea. Anticholinergic drugs (e.g. belladonna, glycopyrrolate, isopropamide) are sometimes co-administered with antacids. The anticholinergic is given to delay emptying of the stomach and so prolong antacid retention. In higher doses, anticholinergic agents will also diminish basal secretion of acid. However such doses are usually accompanied by the undesirable side effects of dry mouth or blurred vision or both. More recently histamine $H_2$ receptor blocking agents (e.g. cimetidine) have found clinical use in the treatment of gastric ulcers. These compounds block histamine $H_2$ effects, including gastric acid secretion and thereby function in the treatment of ulcers. Drugs which function by means other than neutralization or inhibition of secretion of gastric acid have also been reported useful in the treatment of gastric ulcers. One such drug to have gained widespread attention is carbenoxolone sodium, the disodium salt of the hemisuccinate of glycyrrhetinic acid. It is reported to prevent formation of and to accelerate healing of gastric ulcers in animals, including humans. ["A Symposium on Carbenoxolone Sodium" J. M. Robson, F. M. Sullivan, Eds. (Butterworths, London, 1968) 263 pp.]. However, its use is accompanied by undesirable side effects, such as edema, diastolic hypertension or hypokalemia. It cannot be used where cardiovascular, pulmonary or renal reserves are inadequate.

The compounds of the present invention are a further example of a class of antiulcer agents which function in some manner to enhance the normal defense mechanism of the body, rather than to reduce normal body secretions. Many of the present compounds are homologous with known ethyl thiazol-2-ylcarbamoylcarboxylate, a compound reported to have antiallergic activity at a high parenteral dose, and no significant oral activity even at 200 mg./kg. [Sellstedt et al., J. Med. Chem. 18 (9), 926-933 (1975); see also U.S. Pat. No. 3,966,965]. The Sellstedt compound, however, is lacking in the antiulcer activity determined for the compounds of the present invention. Furthermore, unlike ethyl thiazol-2-ylcarbamoylcarboxylate, many of the compounds of the present invention also possess a significant level of oral antiallergy activity. Various 4-phenylthiazol-2-ylcarbamoylcarboxylic acids and esters have been recently reported to be useful as antiallergy agents, [European Patent Appln. 6,368 (Jan. 9, 1980); British Pat. No. 2,023,580 (Jan. 3, 1980)], while certain acylated 2-halothiazol-4-ylamines have been reported useful as antiulcer and hyposecretory agents (Crossley, U.S. Pat. No. 4,183,854).

SUMMARY OF THE INVENTION

It has now been found that certain thiazol-2-ylcarbamoylcarboxylic acids, esters and amides have valuable antiulcer activity. These novel compounds have the formula

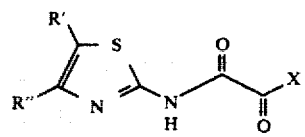

wherein

X is hydroxy, $(C_1-C_5)$-alkoxy, phenoxy, benzyloxy, or $-NH(CH_2)_nY$ wherein n is an integer of value 2 to 4 and Y is di-$(C_1-C_3)$-alkylamino, 1-pyrrolidinyl, 1-piperidinyl or 4-morpholinyl;

R' and R" when taken together are $(C_3-C_8)$-alkylene, with the proviso that the ring so formed is 5- to 8-membered;

R' and R" when taken separately are each independently hydrogen, $(C_1-C_6)$-alkyl or $(C_5-C_6)$-cycloalkyl, with the proviso that when X is other than —NH(CH$_2$)$_n$Y, at least one of R′ and R″ is other than hydrogen;

the pharmaceutically acceptable cationic salts thereof when X is hydroxyl, and the pharmaceutically acceptable anionic salts thereof when X is —NH(CH$_2$)$_n$Y.

The preferred form of the compounds of the present invention is as the (C$_1$-C$_3$)-alkyl esters, the phenyl ester, the benzyl ester or as the amide (—NH(CH$_2$)$_n$Y) wherein n=2 and Y=diethylamino or 4-morpholinyl. The most highly preferred compounds are generally the (C$_1$-C$_3$)-esters, particularly the ethyl ester (I, X=OC$_2$H$_5$). With respect to the substitution of the thiazole ring (R′ and R″), mono- or di-(C$_1$-C$_3$)-alkyl substituted compounds and the (C$_5$-C$_7$)-alkylene compounds are preferred, particularly, the di-(C$_1$-C$_2$)-alkyl and butylene compounds.

The expression "(C$_1$-C$_6$)-alkyl" encompasses such groups as methyl, ethyl, propyl, 2-propyl(isopropyl) 2-methyl-2-propyl(tert-butyl), 2-butyl, 2-methyl-1-propyl(isobutyl), pentyl, etc. The expression "(C$_3$-C$_8$)-alkylene, with the proviso that the ring so formed is 5- to 8-membered" is descriptive of straight chains of 3-6 methylene groups, optionally substituted with alkyl groups, to a maximum of eight carbons, counting both chain and substitutents. For example:

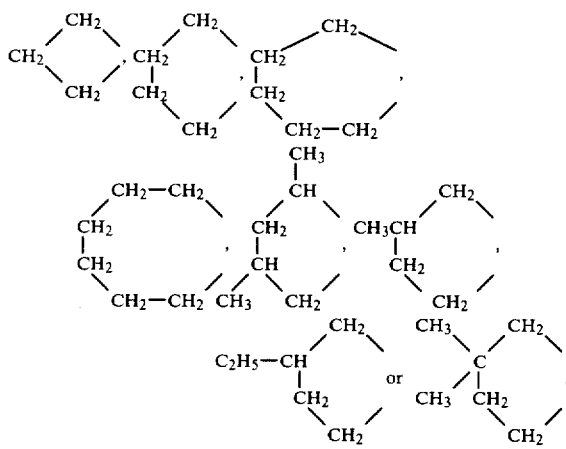

By the expression "pharmaceutically acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as benzathine (N,N′-dibenzylethylenediamine), choline, diethanolamine, ethylenediamine, meglumine (N-methylglucamine), benethamine (N-benzylphenethylamine), diethylamine, piperazine and tromethamine (2-amino-2-hydroxymethyl-1,3-propanediol).

By the expression "pharmaceutically acceptable anionic salts" is intended the pharmaceutically acceptable acid addition salts of the amine function when X is —NH(CH$_2$)$_n$Y. These include, but are not limited to, those formed with hydrochloric, hydrobromic, nitric, phosphoric, sulfuric, benzenesulfonic, citric, laurylsulfonic, fumaric, oxalic, maleic, methanesulfonic, tartaric, p-toluenesulfonic, and succinic acid. With polybasic acids, the salt can include more than one mole of base per mole of acid. However, the acid addition salts which are mole for mole are preferred.

The compounds of this invention are named as derivatives of the following ring systems:

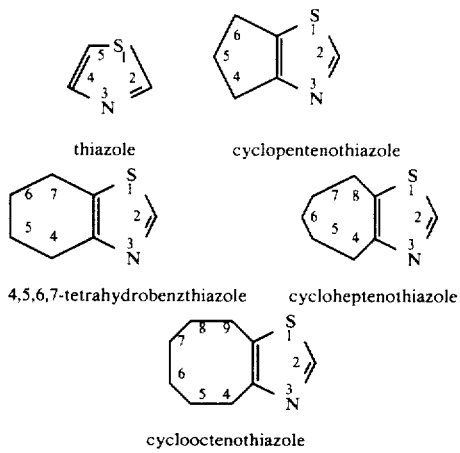

Further, the various compounds are named systematically, rather than as oxalic or oxamic acid derivatives.

The antiulcer activity of the compounds of the present invention is evaluated by an ethanol-induced rat ulcer assay, a test reflecting clinical utility of these compounds in the treatment of peptic ulcers, particularly gastric ulcers.

Many of the compounds of the present invention also possess significant antiallergy activity via the oral route. This activity is determined by the passive cutaneous anaphylaxis (PCA) test [Ovary, J. Immun., 81, 355 (1958)]. This activity is most noteworthy in compounds wherein both R′ and R″ are taken together, or, when taken separately R′ and R″ are both (C$_1$-C$_3$)-alkyl. The preferred use of the compounds however, is as agents for the prevention and treatment of ulcers. Any antiallergy activity which the compounds of the present invention possess does not interfere with their antiulcer activity.

DETAILED DESCRIPTION OF THE INVENTION

The compounds of this invention are readily prepared by the following routes:

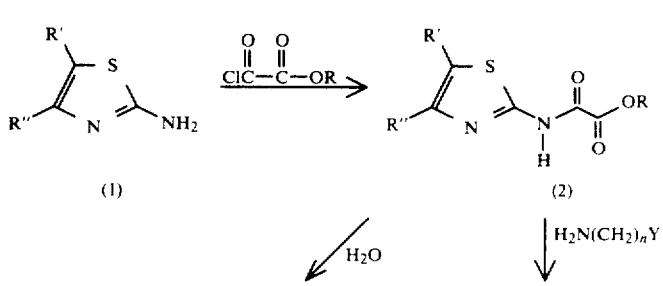

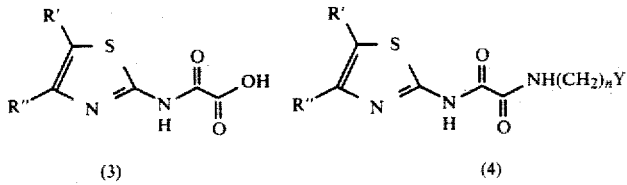

(3)                                      (4)

Wherein n, R', R" and Y are as hereinbefore defined, and R is $(C_1-C_5)$-alkyl, phenyl or benzyl.

The esters (1) are conveniently prepared by acylation of the appropriately substituted 2-aminothiazole with a stoichiometic amount of a $(C_1-C_6)$-alkyl-, phenyl- or benzyl-oxalyl chloride, in the presence of at least an equivalent of base, i.e. sufficient to neutralize the equivalent of hydrogen chloride produced in the reaction. The reaction is conveniently carried out in the presence of an excess of a tertiary amine (e.g. triethylamine, pyridine, N-methylmorpholine), with or without the presence of an inert solvent such as methylene chloride, dioxane, or dimethylformamide. Temperature for the reaction is not critical (e.g. $-50°$ to $50°$ C.). Reaction times are also not critical, although it is preferred that reaction be allowed to proceed to completion (e.g. 5 minutes to 1 hour) depending upon temperature. Completion of reaction is readily determined by use of standard techniques of thin layer chromatography on silica gel. Suitable eluants are chloroform-1% ethanol, or ethyl acetate. Polarity of the eluant can be varied in the standard manner so as to differentiate starting material and product.

When hydrolysis to the acids (3) is desired, the second stage reaction is readily carried out by mild acid or base catalysis. A convenient method for hydrolysis, which minimizes side-reactions, is to warm the ester with one equivalent of aqueous potassium carbonate, with alcohol diluent, if desired, until hydrolysis is substantially complete (e.g. 5 to 30 minutes) on a steam bath. The reaction is conveniently monitored by standard thin layer chromatography methods on silica gel using an eluant such as chloroform/5% acetic acid. When the ester is benzyl, hydrogenolysis over a noble metal catalyst (e.g. 5% Pd/C) in an inert solvent (e.g. water, lower alkanols, dioxane, dimethylformamide, etc.) can be used in place of the hydrolysis step.

When the amides (4) of the present invention are desired, they are conveniently prepared by aminolysis of the corresponding ester with the appropriate diamine. These reactions are generally carried out by reaction of the ester with at least an equimolar amount of the amine. The amine can function as solvent, but it is generally preferred to carry out the reaction in the presence of an inert solvent (e.g. toluene, dioxane, dimethylformamide, etc.). Temperature is not critical (e.g. $0°-150°$ C.), the reaction being allowed to proceed until substantially complete, a factor readily determined by use of thin layer chromatography, as described above. Convenient conditions for this reaction are refluxing toluene for 10–30 minutes.

Many of the requisite 2-aminothiazole starting materials are described in the literature. Those which are not can be prepared by condensation of the appropriate alpha-haloketone with thiourea or by condensation of the appropriate aldehyde with thiourea and sulfuryl chloride, as illustrated in specific examples. Alpha-haloketones, when not described in the literature, are obtained by standard procedures, e.g. by halogenation of ketones [e.g. Catch et al., J. Chem. Soc., 272 (1948); Levine, Org. Synthesis Coll. Vol. II, 38 (1943); Buchman et al., J. Am. Chem. Soc. 67, 400 (1945)]; by the action of hydrogen halides on diazoketones [e.g. Catch et al., J. Chem. Soc., 278 (1948); Lutz et al., J. Org. Chem. 12, 767 (1947); Wagner et al., J. Am. Chem. Soc. 72, 2884 (1950], decarboxylation of alpha-halo-beta-keto acids [McPhee et al., J. Am. Chem. Soc. 66, 1132 (1944)], and the spontaneous cleavage of the dibromo derivatives of alkenyl esters [e.g. Slanina et al., J. Am. Chem. Soc. 58, 891 (1936)].

The $(C_1-C_4)$-alkyl, phenyl or benzyl oxalyl chlorides required for the present syntheses are also available commercially or by methods of the literature (see, for example, Sellstedt et al., U.S. Pat. No. 3,966,965). The requisite diamines are also available commercially or by methods found in the literature, as by reduction of the appropriate nitrile [e.g. reduction of 2-dimethylaminoacetonitrile, Turner, J. Am. Chem. Soc. 68, 1607 (1946)], amination of cyclic amines [e.g. reaction of diethylamine with ethylenimine; Coleman and Callen, J. Am. Chem. Soc. 68, 2006 (1946)], or amino alkylation of phthalimide, followed by hydrolysis [e.g. 2-diethylaminoethylation; Magidson and Grigorowsky, Ber. 69, 396 (1936)].

The pharmaceutically acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness, or by addition of a non-solvent. In some cases, salts can be prepared by mixing a solution of the acid with a solution of a different salt of the cation (e.g. sodium ethylhexanoate, magnesium oleate), employing a solvent in which the desired cationic salt precipitates, or can be otherwise isolated by concentration and/or addition of a non-solvent.

The pharmaceutically acceptable acid addition salts of this invention are readily prepared by contacting the corresponding free base with the appropriate mineral or organic acid in either aqueous solution or in a suitable organic solvent. The salt may then be precipitated by addition of a non-solvent, or by partial evaporation of the solvent. Alternatively, the salt is isolated by freeze drying or evaporation to dryness.

The effectiveness of the products of this invention as antiulcer agents is determined in an ethanol-induced rat ulcer assay. In this test, overnight fasted male rats are orally administered either drug (5 mg./kg.) dissolved or suspended in water or dilute NaOH, or water (controls), fifteen minutes prior to an orally administered dose of absolute ethanol (1.0 ml.). One hour after the ethanol challenge the animals (8/group) are killed and the stomachs examined for the presence of lesions. After sacrifice the abdomen is opened and a locking hemostate placed at the pylorus. Six ml. of a 4% solution of formaldehyde is injected into the stomach with a gastric feeding tube and a second locking hemostate is used to seal the esophagus. The stomach is removed, opened along the greater curvature and examined for ulceration.

The scoring system used to quantitate the ethanol-induced lesions is given below.

| Ulcer Score Table | |
|---|---|
| Score | Definition |
| 1 | Normal appearing stomach |
| 2 | Pinpoint sized lesions |
| 3 | Lesions, 2 or fewer; pinpoint lesions may be present |
| 4 | Lesions, >2; pinpoint lesions may be present |
| 5 | Lesions with hemorrhage |

For each group of animals an ulcer index is calculated as follows:

Ulceration Index=(the sum of the scores of the group)×(the sum of the number of ulcers in the group)×(the fraction of the group having any incidence of ulceration).

The percent inhibition of ulcers is calculated as follows:

% Inhibition=100×[(ulcer index controls)−(ulcer index drug-treated)]÷(ulcer index controls).

Table I shows the activity in this test of various compounds of this invention.

TABLE I

Oral Activity
(% Inhibition at 5 mg./kg. Dosage)
of Compounds of the Formula I
in the Ethanol-Induced Rat Ulcer Assay

| R' | R'' | R | % Inhibition |
|---|---|---|---|
| H | H | $C_2H_5$ | inactive[a] |
| —$(CH_2)_4$— | | $C_2H_5$ | 51 |
| $CH_3$ | $CH_3$ | $C_2H_5$ | 62 |
| $C_2H_5$ | $C_2H_5$ | $C_2H_5$ | 81 |
| H | $CH_3$ | $C_2H_5$ | 48 |
| $CH_3$ | H | $C_2H_5$ | 59 |

[a]The 3% inhibition calculated for this test shows that ulcers in the treated group were not significantly different than those of the control group, and the compound is thus reported as inactive.

The ethanol-induced rat ulcer assay reflects the utility of the compounds of the present invention in the treatment of peptic ulcers in mammals, including man. These products not only accelerate healing of such ulcers, but also prevent their formation. If desired, they can be co-administered with other antiulcer agents.

The valuable compounds of this invention are generally administered with a pharmaceutical carrier. The carrier is selected on the basis of the chosen route of administration and standard pharmaceutical practice. For example, they can be combined with various pharmaceutically acceptable inert carriers in the form of tablets, capsules, lozenges, troches, hard candies, powders, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acid and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically acceptable carriers. Where aqueous suspensions are to be used for oral administration, the compounds of this invention can be combined with emulsifying or suspending agents. Diluents such as ethanol, propylene glycol, glycerin and chloroform and their combinations can be employed as well as other materials.

For the purpose of parenteral administration, solutions or suspensions of these compounds in sesame or peanut oil or aqueous propylene glycol solutions can be employed, as well as sterile aqueous solutions of the soluble pharmaceutically acceptable salts described herein. Where salts are available, these particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

Having full regard for the foregoing factors, it is considered that an effective daily oral dosage of the antiulcer compounds of the present invention in humans is from about 10 to about 1500 mg. per day, with a preferred range of about 10 to about 600 mg. per day in single or divided doses, or at about 0.2 to about 12 mg./kg. of body weight. These values are illustrative and there may, of course, be individual cases where higher or lower dose ranges are merited. With careful supervision, the dosage level can range up to as high as about 2 grams per day.

When administered parenterally, the effective daily dose is from about 0.05 to about 400 mg. per day, and preferably from about 0.25 to 200 mg. per day, or at about 0.005 to 4 mg./kg. of body weight in a single or divided dose.

Administration by the oral route is preferred over parenteral administration, being more convenient and avoiding the possible pain and irritation at the site of injection. However, in circumstances such as where the patient cannot shallow the medication, it is essential that the parenteral route be available as an alternative mode of administration. Obviously, more than one dosage form can be administered at about the same time.

The present invention is illustrated by the following examples. However, it should be understood that the invention is not limited to the specific details of these examples.

EXAMPLE 1

2-Amino-4-ethyl-5-methylthiazole

Thiourea (20.9 g., 0.275 mole) was dissolved in 250 ml. of refluxing ethanol. 2-Bromo-3-pentanone (41.3 g., 0.25 mole), dissolved in 50 ml. of ethanol, was added dropwise over 25 minutes to the refluxing thiourea solution. Following an additional 2 hours of reflux, the reaction was boiled down to approximately 100 ml., cooled and the crude product recovered as the hydrobromide salt by filtration. Purified 2-amino-4-ethyl-5-methylthiazole (15.1 g.; m.p. 45°–50° C.; m/e calcd: 142; found: 142) was obtained by dissolution in water and reprecipitation with aqueous 3 N potassium hydroxide.

By the same method, 1-bromo-2-heptanone, 3-bromo-4-heptanone and 4-bromo-2,5-dimethyl-3-hexanone are converted to 2-amino-4-pentylthiazole, 2-amino-4-ethyl-5-propylthiazole and 2-amino-4,5-diisopropylthiazole, respectively.

EXAMPLE 2

2-Amino-4,5-diethylthiazole hydrochloride

Thiourea (21.8 g., 0.286 mole), 4-chloro-3-hexanone (34.4 g., 0.26 mole) and 200 ml. of ethanol were combined and heated to reflux for 19 hours. The reaction mixture was cooled and stripped of solvent to yield the crude product as a white solid. White crystals of 4,5-diethylthiazole hydrochloride (31 g., m.p. 154°–156° C.) were obtained by recrystallization from a mixture of ethyl acetate and ethanol.

EXAMPLE 3

2-Aminocycloheptenothiazole

Thiourea (41.9 g., 0.55 mole), 2-chlorocycloheptanone (72.3 g., 0.49 mole) and 500 ml. of ethanol were combined and refluxed for 7 hours. The solvent was stripped, leaving a semi-solid which was distributed between ethyl acetate and water. Unreacted chloroketone, recovered from the ethyl acetate phase by stripping, was combined with 20 g. of thiourea and ethanol, refluxed for 24 hours, stripped and additional crude product distributed between ethyl acetate and water as above. In each case, product was recovered by making the aqueous phase basic with ammonium hydroxide, extraction into ethyl acetate, drying over anhydrous sodium sulfate, stripping to an oil, solidification by trituration with hexane and filtration. Purified 2-aminocycloheptenothiazole (49.5 g., m.p. 77°–85.5° C.) was obtained by recrystallization from cyclohexane.

EXAMPLE 4

2-Amino-4-isopropylthiazole

Thiourea (52.5 g., 0.69 mole) was slurried in 400 ml. of ethanol. 1-Bromo-3-methyl-2-butanone (109.5 g., 0.66 mole) was added to the slurry. The resulting exothermic reaction caused dissolution and reflux. Reflux was maintained by external heating for one hour. Solvent was removed by boiling and stripping to yield an oil which crystallized on standing. Final purification of 2-amino-4-isopropylthiazole hydrobromide (104.4 g., m.p. 74°–76° C.) was achieved by trituration with ether.

The hydrobromide salt was converted to free base (58.6 g.) by dissolving the salt in water, basifying with excess ammonium hydroxide, extracting the free base into ether, drying the ether over anhydrous sodium sulfate and stripping to an oil.

EXAMPLE 5

2-Amino-4-cyclohexylthiazole

Cyclohexylbromomethylketone (49 g., 0.24 mole) was added to a slurry of thiourea (20.1 g., 0.26 mole) in 250 ml. of ethanol and the mixture heated to reflux. The resulting solution was refluxed for 2 hours, cooled to room temperature and evaporated in vacuo to an oil. The oil was taken up in 100 ml. of water, the solution made basic with concentrated ammonium hydroxide and crude product recovered in two crops by filtration. Crude product was recrystallized from cyclohexane to yield purified 2-amino-4-cyclohexylthiazole (20.4 g.; m.p. 141°–143° C.).

EXAMPLE 6

2-Amino-4,5,6,7-tetrahydro-6-methylbenzthiazole

Thiourea (22.3 g., 0.29 mole) was slurried in 275 ml. of ethanol. 2-Bromo-4-methylcyclohexanone was added and the mixture heated to reflux for 75 minutes. The reaction mixture was cooled to room temperature and the crude product recovered as the hydrobromide salt by filtration. The crude salt was dissolved in warm water, filtered and made basic with ammonium hydroxide to precipitate the free base as an oil, which crystallized on cooling. Purified 2-amino-4,5,6,7-tetrahydro-6-methylbenzthiazole (25.2 g., m.p. 98°–100° C.) was obtained by recrystallization from cyclohexane.

EXAMPLE 7

2-Amino-6,6-dimethyl-4,5,6,7-tetrahydrobenzthiazole

2-Amino-6,6-dimethyl-4,5,6,7-tetrahydrobenzthiazole (9.8 g., m.p. 109°–111° C.) was made from thiourea (9.2 g., 0.12 mole) and 2-bromo-4,4-dimethylcyclohexanone (22.6 g., 0.11 mole) in 100 ml. of ethanol according to the method of Example 6.

EXAMPLE 8

2-Amino-4-(2-butyl)thiazole

Thiourea (16.7 g., 0.22 mole), 1-bromo-3-methyl-2-pentanone (36 g., 0.2 mole) and 100 ml. of ethanol were combined and heated to reflux for 5 hours. Aqueous potassium hydroxide (3 N, 100 ml.) was added and reflux continued for an additional 0.5 hour. The reaction mixture was cooled, acidified with hydrochloric acid and nonbasic impurities extracted away with ether. The aqueous phase was made basic with ammonium hydroxide and the product extracted into ether. Following back-wash with water and drying over anhydrous sodium sulfate, the ether was stripped to yield 10 g., of 2-amino-4-(2-butyl)thiazole as a dark brown viscous oil.

EXAMPLE 9

2-Aminocyclooctenothiazole

Thiourea (11.2 g., 0.147 mole) was slurried in 150 ml. of ethanol and heated to reflux to yield a clear solution. Under continued reflux, 2-bromocyclooctanone (27.6 g., 0.134 mole), dissolved in 50 ml. of ethanol, was added over 15 minutes. Reflux was continued for 4 hours. A minor amount of precipitate, which occurred during reflux, was removed by filtration, as was a further precipitate which occurred on cooling. The mother liquor was stripped to a semi-solid, which was taken into 225 ml. of water in divided portions. The resulting aqueous solution was made basic with excess concentrated ammonium hydroxide and the product extracted into 200 ml. of methylene chloride. The organic layer was back-washed with water, then washed with saturated sodium chloride, dried over anhydrous magnesium sulfate, filtered and stripped to an oil. The oil was triturated with hexane and crystallization induced by scratching. Recrystallization from hot hexane produced purified 2-aminocyclootenothiazole (9.13 g.; m.p. 59°-61° C.; literature m.p. 56°-58° C.).

EXAMPLE 10

2-Amino-4,5,6,7-tetrahydrobenzthiazole

Thiourea (123.3 g., 1.62 moles) was combined with 400 ml. of dimethylformamide and heated on a steam bath. After dissolution of the thiourea was complete, 2-chlorocyclohexanone (195.1 g., 1.47 moles) was added dropwise over 20 minutes, during which the temperature began to rise above 100° C., and external heating was discontinued. The temperature rose to a maximum of 128° C. After addition was complete, heating on the steam bath was resumed and was continued for 30 minutes. The reaction mixture was cooled to 5° C. and crude product recovered by filtration. The crude was partially dried to 242.4 g., and then dissolved by warming in a mixture of 1.4 l. of water, 100 ml. of methanol and 50 ml. of concentrated hydrochloric acid. The acidic solution was added dropwise to a stirred mixture of 150 ml. of concentrated ammonium hydroxide and ice and partially purified product (167.6 g.) recovered by filtration. Recrystallization from 1400 ml. of cyclohexane gave purified 2-aminio-4,5,6,7-tetrahydrobenzthiazole (150 g., m.p. 86°-87° C.).

EXAMPLE 11

2-Aminocyclopentenothiazole

2-Chlorocyclopentanone (72.6 g., 0.61 mole), thiourea (46.0 g., 0.61 mole) and dimethylformamide (250 ml.) were combined and heated on a steam bath for forty minutes. The reaction mixture was cooled and 2-aminocyclopentenothiazole hydrochloride [92.4 g.; m.p. 260°-261° C. (dec.)] recovered by filtration.

Analysis Calcd. for $C_8H_8N_2S.HCl$: C, 40.79; H, 5.14; N, 15.86. Found: C, 40.91; H, 5.21; N, 16.21.

EXAMPLE 12

2-Amino-5-methylthiazole

Thiourea (45.7 g., 0.6 mole) and propionaldehyde (7.4 g., 0.3 mole) were combined with 150 ml. of chloroform and cooled in an ice bath. Sulfuryl chloride (44.5 g., 0.33 mole) was added over 15 minutes. The exothermic reaction was maintained between 15° and 24° C. Gassing, which occurred during addition, ceased about 1 hour after addition was complete. Most of the chloroform was boiled off on a steam bath. Ethanol (150 ml.) was added and the mixture refluxed for 3 hours.

The reaction was stripped to an oil, which was distributed between water and ethyl acetate. The aqueous phase was made basic with ammonium hydroxide and the product extracted into fresh ethyl acetate. The ethyl acetate was dried over anhydrous sodium sulfate and stripped to yield crude product as a white solid. Purified 2-amino-5-methylthiazole (8.36 g., m.p. 94°-95° C.) was obtained by recrystallization from cyclohexane.

EXAMPLE 13

2-Amino-5-ethylthiazole

Thiourea (45.7 g., 0.6 mole) and butyraldehyde (21.6 g., 0.3 mole) were combined with 150 ml. of chloroform and cooled in an ice bath. Sulfuryl chloride (44.5 g., 0.33 mole) was added over 15 minutes. The exothermic reaction was maintained between 15° and 25° C. Gassing occurred during addition and for about 1 hour thereafter. Ethanol (400 ml.) was added, the chloroform was boiled off and the reaction mixture refluxed overnight (approximately 16 hours). The reaction was stripped to an oil and recrystallized 2-amino-5-ethylthiazole (11.7 g., m.p. 54°-55° C.) isolated by the method of Example 9.

By the same method, pentanal, 3-methylbutanal and heptanal are converted to 2-amino-5-propylthiazole, 2-amino-5-isopropylthiazole and 2-amino-5-pentylthiazole, respectively.

EXAMPLE 14

Ethyl 4-Methylthiazol-2-ylcarbamoylcarboxylate

2-Amino-4-methylthiazole (5 g., 43.8 mmoles) was combined with 35 ml. of pyridine and gently heated to achieve dissolution. The solution was cooled in an ice-water bath and ethyloxalylchloride added dropwise over 10 minutes. The reaction mixture was then stirred for 45 minutes at room temperature, at which time tlc (chloroform-1% ethanol) indicated conversion was complete. The reaction mixture was poured into about 150 ml. of ice-water, and product (8.8 g., m.p. 171°-173° C.) recovered by filtration. Recrystallization from isopropyl alcohol afforded ethyl 4-methylthiazol-2-ylcarbamoylcarboxylate (6.6 g., 172°-174° C.).

Analysis Calcd. for $C_8H_{10}O_3N_2S$: C, 44.85; H, 4.70; N, 13.08; m/e, 214. Found C, 45.30; H, 4.80; N, 13.22; m/e, 214.

EXAMPLE 15

Ethyl 5-Methylthiazol-2-ylcarbamoylcarboxylate

2-Amino-5-methylthiazole (3.0 g., 26.3 mmoles) was dissolved in 25 ml. of pyridine and the solution cooled in an ice-water bath. Ethyloxalyl chloride (3 ml., 26.9 mmoles) was added dropwise over 10 minutes. The reaction mixture was stirred at room temperature for 20 minutes, and then poured into about 50 ml. of ice-water to precipitate product (4.1 g., m.p. 167°-169° C.). Recrystallization from isopropyl alcohol gave essentially quantitative recovery of ethyl 5-methylthiazol-2-ylcarbamoylcarboxylate (m.p. 166.5°-168.5° C.).

Analysis Calcd. for $C_8H_{10}O_3N_2S$: C, 44.85; H, 4.70; N, 13.07. Found: C, 44.53; H, 4.73; N, 13.00.

EXAMPLE 16

Ethyl 4,5-Dimethylthiazol-2-ylcarbamoylcarboxylate

2-Amino-4,5-dimethylthiazole hydrobromide (8 g., 38.3 mmoles) was slurried in 50 ml. of pyridine and the mixture chilled in an ice-water bath. Ethyloxalyl chloride (4.3 ml., 38.5 mmoles) was added dropwise over 10 minutes. After addition was complete, the reaction was stirred at room temperature for 30 minutes. The heterogeneous reaction mixture was stripped to solids which were taken up in about 75 ml. of water and the product extracted into 75 ml. of ethyl acetate. The ethyl acetate layer was back-washed with 75 ml. of saturated sodium chloride, dried over anhydrous sodium sulfate, filtered and stripped to an oil which was crystallized by the addition of hexane and scratching. Crude product (6.0 g., m.p. 86°–88° C.) was recrystallized from hexane to yield purified ethyl 4,5-dimethylthiazol-2-ylcarbamoylcarboxylate (3.54 g., m.p. 87°–89° C.).

Analysis Calcd. for $C_9H_{12}O_3N_2S$: C, 47.36; H, 5.30; N, 12.27. Found: C, 47.10; H, 5.30; N, 12.36.

EXAMPLE 17

Ethyl 5-Ethylthiazol-2-ylcarbamoylcarboxylate

2-Amino-5-ethylthiazole (3.2 g., 25 mmoles) was dissolved in 20 ml. of pyridine and cooled in an ice-water bath. Ethyloxalyl chloride (3.8 g., 28 mmoles) was added dropwise over 10 minutes. The mixture was stirred for an additional 15 minutes at 0°–5° C., and then for 0.5 hour at room temperature. Thin layer chromatography (chloroform-1% ethanol as eluant) indicated reaction was complete. The mixture was diluted with circa 75 ml. of ice-water and crude product (5 g.) recovered by filtration. Recrystallization from 65-70 ml. of isopropyl alcohol gave purified ethyl 5-ethylthiazol-2-ylcarbamoylcarboxylate (4.5 g., m.p. 121°–122° C.).

Analysis Calcd. for $C_9H_{12}O_3N_2S$: C, 47.35; H, 5.30; N, 12.27. Found: C, 47.44; H, 5.35; N, 12.37.

EXAMPLE 18

Ethyl 4,5-Diethylthiazol-2-ylcarbamoylcarboxylate

2-Amino-4,5-diethylthiazole hydrochloride (2.9 g., 15 mmoles) was slurried in 20 ml. of pyridine and cooled in an ice-water bath. Ethyloxalyl chloride (2.3 g., 1.9 ml., 17 mmoles) was added dropwise over 10 minutes. The reaction was stirred for 15 minutes in the ice-water bath and then for 30 minutes at room temperature. The reaction mixture was diluted with approximately 70 ml. of ice and water and the oily precipitate which formed extracted into chloroform (2×75 ml.). The combined chloroform extracts were dried over anhydrous sodium sulfate, filtered and stripped in vacuo to an oil, which was crystallized by triturating and stirring with 40 ml. of water. Approximately 3 g. of crude product resulted. Recrystallization from approximately 30 ml. of cyclohexane gave purified ethyl 4,5-diethylthiazol-2-ylcarbamoylcarboxylate (1.8 g., m.p. 71.5°–72.5° C.).

Analysis Calcd. for $C_{11}H_{16}O_3N_2S$: C, 51.54; H, 6.29; N, 10.93. Found: C, 51.86; H, 6.18; N, 11.15.

EXAMPLE 19

Ethyl 4-(2-Propyl)thiazol-2-ylcarbamoylcarboxylate

2-Amino-4-(2-propyl)thiazole (5.0 g.; 35.2 mmoles) was dissolved in 35 ml. of pyridine and cooled in an ice-water bath. Ethyloxalyl chloride (4.0 ml., 35.8 mmoles) was added dropwise over 10 minutes. The resulting slurry was stirred for 30 minutes at room temperature, at which time tlc (chloroform-1% ethanol) indicated reaction was complete. The mixture was evaporated in vacuo to an oil. The oil was distributed between water and ethyl acetate. The ethyl acetate layer was separated, back-washed with saturated sodium chloride, dried over anhydrous sodium sulfate, filtered and re-evaporated to an oil (8.1 g.). The oil was distilled (b.p. 135°–145° C./0.3 mm.). The distillate, which crystallized on scratching, was triturated with hexane, yielding solid product (3.2 g., m.p. 54°–57° C.). Recrystallization from petroleum ether gave purified ethyl 4-(2-propyl)thiazol-2-ylcarbamoylcarboxylate (2.06 g., m.p. 57°–59° C.).

Analysis Calcd. for $C_{10}H_{14}O_3N_2S$: C, 49.57; H, 5.82; N, 11.56; m/e, 242. Found: C, 49.21; H, 5.91; N, 11.54; m/e, 242.

EXAMPLE 20

Ethyl 4-(2-Methyl-2-propyl)-thiazol-2-ylcarbamoylcarboxylate

2-Amino-4-(2-methyl-2-propyl)thiazole (5 g., 32 mmoles) was dissolved in 35 ml. of pyridine and cooled in an ice-water bath. Ethyloxalyl chloride (3.6 ml., 32.2 mmoles) was added dropwise over 10 minutes. After stirring for 20 minutes at room temperature, tlc (chloroform-1% ethanol) indicated incomplete reaction. The mixture was recooled, and additional ethyloxalyl chloride (1.8 ml.) added dropwise over 5 minutes. After further stirring at room temperature for 15 minutes, tlc indicated that reaction was complete. The mixture was poured into about 100 ml. of ice-water and crude product, having a tendency to oil, recovered by filtration. The crude product was taken up in ether, and the ether washed with dilute hydrochloric acid, dried over anhydrous sodium sulfate, filtered and reevaporated to an oil. Distillation gave purified ethyl 4-(2-methyl-2-propyl)thiazol-2-ylcarbamoylcarboxylate (5.9 g., b.p. 139°–150° C./0.5–0.7 mm.).

Analysis Calcd. for $C_{11}H_{16}N_2O_3S$: C, 51.55; H, 6.29; N, 10.93. Found: C, 51.21; H, 6.22; N, 11.05.

EXAMPLE 21

Ethyl 4-Cyclohexylthiazol-2-ylcarbamoylcarboxylate

2-Amino-4-cyclohexylthiazole (3 g., 16.5 mmoles) was dissolved in 25 ml. of pyridine and cooled in an ice-water bath. Ethyloxalyl chloride (2 ml., 17.9 mmoles) was added dropwise over 5 minutes. The mixture was warmed and allowed to stir at room temperature for 15 minutes, at which time thin layer chromatography (chloroform-1% ethanol) indicated incomplete reaction. The mixture was again cooled and a further 2 ml. of ethyloxalyl chloride added over 10 minutes. After stirring for 15 minutes at room temperature, tlc indicated reaction was complete. Crude product (4.9 g.) was precipiated by pouring the reaction mixture into 100 ml. of ice water. Recrystallization from hexane afforded purified ethyl 4-cyclohexylthiazol-2-ylcarbamoylcarboxylate (2.5 g.; m.p. 45°–47° C.).

Analysis Calcd. for $C_{13}H_{18}O_3N_2S$: C, 55.30; H, 6.43; N, 9.92; m/e 282. Found: C, 54.96; H, 6.28; N, 10.06; m/e 282.

EXAMPLE 22

Ethyl Cyclopentenothiazol-2-ylcarbamoylcarboxylate

2-Aminocyclopentenothiazole (2.6 g., 15 mmoles) was slurried in 25 ml. of pyridine and cooled in an ice-water bath. Ethyloxalyl chloride (2.3 g., 1.9 ml., 17 mmoles was added dropwise over 10–15 minutes. The reaction mixture was stirred in the cooling bath for 15 minutes and then at room temperature for 30 minutes. The reaction mixture was diluted with approximately 65 ml. of water and ethyl cyclopentenothiazol-2-ylcarbamoylcarboxylate (2.33 g., m.p. 123.5°–124.5° C.) recovered by filtration.

Analysis Calcd. for $C_{10}H_{12}O_3N_2S$: C, 49.98; H, 5.04; N, 11.66. Found: C, 50.25; H, 4.83; N, 11.91.

EXAMPLE 23

Ethyl 4,5,6,7-Tetrahydrobenzthiazol-ylcarbamoylcarboxylate

2-Amino-4,5,6,7-tetrahydrobenzthiazole (3.1 g., 20 mmoles) was dissolved in 20 ml. of pyridine and cooled in an ice-water bath. Ethyloxalyl chloride (3.0 g., 2.5 ml., 22 mmoles) was added dropwise over 10 minutes. Some precipitation occurred. The reaction mixture was stirred for 15 minutes in the cooling bath and then for 30 minutes at room temperature. The reaction mixture was diluted with approximately 100 ml. of ice-water and ethyl 4,5,6,7-tetrahydrobenzthiazol-2-ylcarbamoylcarboxylate (4.1 g., m.p. 119°–122° C.) recovered by filtration.

Analysis Calcd. for $C_{11}H_{14}O_3N_2S$: C, 51.95; H, 5.55; N, 11.02. Found: C, 52.07; H, 5.50; N, 11.26.

EXAMPLE 24

Ethyl Cycloheptenothiazol-2-ylcarbamoylcarboxylate

2-Aminocycloheptenothiazole (2.5 g., 15 mmoles) was dissolved in 25 ml. of pyridine and cooled in an ice-water bath. Ethyloxalyl chloride (2.3 g., 1.9 ml., 17 mmoles) was added dropwise over approximately 10 minutes, at which time a precipitate began to form. The reaction mixture was stirred for 15 minutes in the cold bath and then for 30 minutes at room temperature. The reaction mixture was added to approximately 100 ml. of ice-water, precipitating additional product which was recovered by filtration. Recrystallization of the crude from approximately 75 ml. of isopropyl alcohol gave purified ethyl cycloheptenothiazol-2-ylcarbamoylcarboxylate (3.5 g.; m.p. 168.5°–169.5° C.).

Analysis Calcd. for $C_{12}H_{16}O_3N_2S$: C, 53.71; H, 6.01; N, 10.44. Found: C, 53.59; H, 5.91; N, 10.46.

EXAMPLE 25

Ethyl Cyclooctenothiazol-2-ylcarbamoylcarboxylate

2-Aminocyclooctenothiazole (2.0 g., 11.0 mmoles) was dissolved in 15 ml. of pyridine and cooled in an ice-water bath. Ethyloxalyl chloride (1.3 ml., 11.6 mmoles) was added dropwise over 5 minutes and the mixture warmed to room temperature and stirred for 1 hour. Since thin layer chromatography (chloroform/1% ethanol as eluant) indicated incomplete reaction, the mixture was recooled and additional ethyloxalyl chloride (0.6 ml., 5.4 mmoles) added dropwise. After warming to room temperature and stirring for an additional 15 minutes, the reaction mixture was stripped to an oil. The oil was crystallized by trituration with water. Recrystallization from cyclohexane gave purified ethyl cyclooctenothiazol-2-ylcarbamoylcarboxylate (1.88 g., m.p. 113°–115° C.).

Analysis Calcd. for $C_{13}H_{18}N_2O_3S$: C, 55.30; H, 6.42; N, 9.92; m/e 282. Found: C, 55.18; H, 6.36; N, 9.86; m/e 282.

By the method of Examples 14–25, methyloxalyl chloride, propyloxalyl chloride, isopropyloxalyl chloride, hexyloxalyl chloride, phenyloxalyl chloride, benzyloxalyl chloride, etc., is substituted for ethyloxalyl chloride to produce the corresponding methyl, propyl, isopropyl, hexyl, phenyl, benzyl, etc., esters.

By the method of Examples 14–25, the other 2-aminothiazoles of Examples 1–13 are converted to the corresponding ($C_1$–$C_6$)-alkyl, phenyl and benzylthiazol-2-ylcarbamoylcarboxylates, e.g.:

methyl 4-pentylthiazol-2-ylcarbamoylcarboxylate;
propyl 4-ethyl-5-propylthiazol-2-ylcarbamoylcarboxylate;
2-propyl 4,5-di(2-propyl)thiazol-2-ylcarbamoylcarboxylate;
hexyl 6-methyl-4,5,6,7-tetrahydrobenzthiazol-2-ylcarbamoylcarboxylate;
phenyl 6,6-dimethyl-4,5,6,7-tetrahydrobenzthiazol-2-ylcarbamoylcarboxylate; and
benzyl 2-butylthiazol-2-ylcarbamoylcarboxylate.

EXAMPLE 26

4-Methylthiazol-2-ylcarbamoylcarboxylic Acid

Ethyl 4-methylthiazol-2-ylcarbamoylcarboxylate (5 g., (23.3 mmoles) was slurried in 200 ml. of water. Potassium carbonate 23.2 ml. of 1 N) was added and the mixture heated on a steam bath for 15 minutes (after 10 minutes tlc indicated reaction almost complete). The reaction mixture was clarified by filtration, cooled and product (2.4 g.) precipitated by acidification with acetic acid. Recrystallization from dimethylformamide gave purified 4-methylthiazol-2-ylcarbamoylcarboxylic acid [1.39 g., m.p. 239°–241° C. (dec.)].

Analysis Calc.d for $C_6H_6O_3N_2S$: C, 38.71; H, 3.35; N, 15.05; m/e, 186. Found: C, 38.73; H, 3.36; N, 15.10; m/e, 186.

EXAMPLE 27

5-Methylthiazol-2-ylcarbamoylcarboxylic Acid

Ethyl 5-methylthiazol-2-ylcarbamoylcarboxylate (3 g., 14 mmole) was combined with 120 ml. of water and 14 ml. of 1N potassium carbonate and heated on a steam bath for 10 minutes. The mixture was clarified by filtration, cooled in an ice-water bath, acidified with acetic acid, filtered to yield a first crop of product (400 mg.) and evaporated to yield a second crop of product (1.45 g.). The two crops were recrystallized from acetic acid affording purified 5-methylthiazol-2-ylcarbamoylcarboxylic acid [1.12 g., m.p. 212°–213° C. (dec.)].

Analysis Calcd. for $C_6H_6O_3N_2S$: C, 38.71; H, 3.25; N, 15.05. Found: C, 38.43; H, 3.31; N, 14.97.

EXAMPLE 28

4,5-Dimethylthiazol-2-ylcarbamoylcarboxylic Acid

Ethyl 4,5-dimethylthiazol-2-ylcarbamoylcarboxylate (1.2 g., 5.26 mmole) was slurried in 40 ml. of water. Potassium carbonate (1 N, 5.3 ml., 2.65 mmoles) was added and the mixture heated on a steam bath for 5 minutes, yielding a clear solution. The reaction mixture was cooled in an ice-water bath and 6 ml. of 1 N hydrochloric acid added. The precipitated crude product was recovered by filtration (933 mg.). Recrystallization from acetic acid gave purified 4,5-dimethylthiazol-2-ylcarbamoylcarboxylic acid [652 mg.; m.p. 235°–236° C. (dec.)].

Analysis Calcd. for $C_7H_8O_3N_2S$: C, 41.99; H, 4.03; N, 13.99. Found: C, 41.76; H, 4.11; N, 13.78.

EXAMPLE 29

5-Ethylthiazol-2-ylcarbamoylcarboxylic Acid

Ethyl 5-ethylthiazol-2-ylcarbamoylcarboxylate (685 mg., 3 mmoles), 1 N potassium carbonate (3 ml., 3 equivalents), water (22 ml.) and ethanol (2—3 ml.) were heated on a steam bath. After 10 minutes, dissolution was nearly complete. After an additional 15 minutes, tlc (chloroform-5% acetic acid) indicated reaction was complete. The cooled reaction mixture was filtered, and crude product (380 mg.) precipitated from the filtrate by acidification with acetic acid. Recrystallization of the crude from isopropyl alcohol gave purified 5-ethylthiazol-2-ylcarbamoylcarboxylic acid [280 mg., m.p. 206.5° C. (dec)].

Analysis Calcd. for $C_7H_8O_3N_2S$: C, 41.99; H, 4.02; N, 13.99. Found: C, 42.04; H, 4.03; N, 14.16.

EXAMPLE 30

4,5-Diethylthiazol-2-ylcarbamoylcarboxylic Acid

Ethyl 4,5-diethylthiazol-2-ylcarbamoylcarboxylate (897 mg., 3.5 mmoles), 1 N potassium carbonate (3.5 ml., 3.5 equivalents) and 27 ml. of water were combined and heated on a steam bath for 10 minutes. Clear solution was noted after 5 minutes. The reaction mixture was cooled and made acidic with acetic acid. Crude product (625 mg.) was recovered by filtration. Recrystallization from approximately 33 ml. of absolute ethanol gave purified 4,5-diethylthiazol-2-ylcarbamoylcarboxylic acid [470 mg.; m.p. 206° C. (dec.)].

Analysis Calcd. for $C_9H_{12}O_3N_2S$: C, 47.35; H, 5.30; N, 12.27. Found: C, 47.32; H, 5.30; N, 12.22.

EXAMPLE 31

4-(2-Propyl)thiazol-2-ylcarbamoylcarboxylic Acid

Ethyl 4-(2-propyl)thiazol-2-ylcarbamoylcarboxylate was combined with 50 ml. of water and 6.2 ml. of 1 N potassium carbonate. The mixture was clarified, cooled, acidified with acetic acid and product extracted into 150 ml. of ethyl acetate in three portions. The combined extracts were dried over anhydrous sodium sulfate, filtered and evaporated to an oil, which partially crystallized on standing. The gummy solid was recrystallized from isopropyl alcohol, affording 4-(2-propyl)thiazol-2-ylcarbamoylcarboxylic acid [216 mg.; m.p. 195°-197° C. (dec.)].

Analysis Calcd. for $C_8H_{10}N_2O_3S$: C, 44.85; H, 4.70; N, 13.07. Found: C, 44.66; H, 4.86; N, 12.62.

EXAMPLE 32

4-(2-methyl-2-propyl)thiazol-2-ylcarbamoylcarboxylic Acid

Ethyl 4-(2-methyl-2-propyl)thiazol-2-ylcarbamoylcarboxylate (1.3 g., 5 mmoles) was combined with 40 ml. of water, 20 ml. of ethanol and 5 ml. of 1 N potassium carbonate and the mixture heated on a steam bath for 10 minutes. Completion of reaction was determined by tlc. The solution was stripped of ethanol and the aqueous residue clarified by filtration. The filtrate was cooled in an ice-water bath and the product (1.02 g.) precipitated by acidification with 1 N hydrochloric acid. Recrystallization from ethyl acetate provided purified 4-(2-methyl-2-propyl)thiazol-2-ylcarbamoylcarboxylic acid [0.72 g.; m.p. 198°-200° C. dec.)].

Analysis Calcd. for $C_9H_{12}N_2O_3S$: C, 47.36; H, 5.30; N, 12.27. Found: C, 47.38; H, 5.19; N, 12.31.

EXAMPLE 33

4-Cyclohexylthiazol-2-ylcarbamoylcarboxylic Acid

Ethyl 4-cyclohexylthiazol-2-ylcarbamoylcarboxylate (1.41 g., 5 mmole) was combined with 40 ml. of water and 5 ml. of 1 N potassium carbonate (1 equivalent, 2.5 mmole) was heated on a steam bath for 15 minutes. After 10 minutes, tlc (chloroform-1% ethanol) indicated hydrolysis was almost complete. The hot reaction mixture was clarified by filtration, cooled in an ice-water bath and acidified with 10.5 ml. of 1 N hydrochloric acid. Product (1.02 g.) was recovered by filtration. Recrystallization from isopropyl alcohol gave purified 4-cyclohexylthiazol-2-ylcarbamoylcarboxylic acid [625 mg.; m.p. 198.5°-200.5° C. (dec)].

Analysis Calcd. for $C_{11}H_{14}N_2O_3S$: C, 51.95; H, 5.55; N, 11.01. Found: C, 52.00; H, 5.55; N, 11.02.

EXAMPLE 34

Cyclopentenothiazol-2-ylcarbamoylcarboxylic Acid

Ethyl cyclopentenothiazol-2-ylcarbamoylcarboxylate (961 mg., 4.0 mmoles), potassium carbonate (1 N, 4 ml., 2.0 mmoles) and 33 ml. of water were combined and heated on a steam bath for 10 minutes; a clear solution was noted after 5 minutes. The reaction mixture was cooled, acidified with acetic acid, and crude product (430 mg.) recovered by filtration. Recrystallization from approximately 30 ml. of acetic acid gave purified cyclopentenothiazol-2-ylcarbamoylcarboxylic acid [310 mg.; m.p. 219.5° C. (ded)].

Analysis Calcd. for $C_8H_8O_3N_2S$: C, 45.27; H, 3.80; N, 13.20. Found: C, 45.23; H, 3.93; N, 13.27.

EXAMPLE 35

4,5,6,7-Tetrahydrobenzthiazol-2-ylcarbamoylcarboxylic Acid

Ethyl 4,5,6,7-tetrahydrobenzthiazol-2-ylcarbamoylcarboxylate 81.27 g., 5.0 mmoles), potassium carbonate (1 N, 5 ml., 2.5 mmoles) and 40 ml. of water were combined and heated on a steam bath. Dissolution was nearly complete with 5 minutes. The mixture was heated for an additional 15 minutes and a small amount of insoluble materials removed by hot filtration. The filtrate was cooled, acidified with acetic acid and crude product recovered by filtration. The crude was recrystallized from approximately 10 ml. of dimethylformamide and 5 ml. of water to yield purified 4,5,6,7-tetrahydrobenzthiazol-2-ylcarbamoylcarboxylic acid [510 mg., m.p. 224.5° C. (dec.)].

Analysis Calcd. for $C_9H_{10}O_3N_2S$: C, 47.77; H, 4.46; N, 12.38. Found: C, 48.09; H, 4.37; N, 12.78.

EXAMPLE 36

Cycloheptenothiazol-2-ylcarbamoylcarboxylic Acid

Ethyl cycloheptenothiazol-2-ylcarbamoylcarboxylate (268 mg., 1.0 mmole), potassium carbonate (1 N, 1 ml., 0.5 mmole) and 9 ml. of water were combined and heated for 1.5 hour on a steam bath. A small amount of insoluble material was removed by filtration of the hot solution. The filtrate was cooled and made acidic with acetic acid. The precipitated crude product (approximately 115 mg.) was recovered by filtration. Recrystallization of the crude from approximately 5 ml. of dimethylformamide and 0.5 ml. of water yielded purified cycloheptenothiazol-2-ylcarbamoylcarboxylic acid [94 mg., m.p. 213° C. (dec)].

Analysis Calcd. for $C_{10}H_{12}O_3N_2S$: C, 49.98; H, 5.04; N, 11.66. Found: C, 49.97; H, 4.88; N, 11.79.

EXAMPLE 37

Cyclooctenothiazol-2-ylcarbamoylcarboxylic Acid

Ethyl cyclooctenothiazol-2-ylcarbamoylcarboxylate (1.1 g., 3.9 mmoles) was combined with 40 ml. of water and 3.9 ml. of 1 N potassium carbonate (1.95 mmoles). The mixture was heated on a steam bath for 10 minutes.

The mixture was filtered while warm to remove a trace of insoluble material. The filtrate was cooled in an ice-water bath and made acidic with acetic acid. Crude product (732 mg.) was recovered by filtration. The crude was recrystallized from approximately 15 ml. of dimethylformamide and 3 ml. of water, yielding purified cyclooctenothiazol-2-ylcarbamoylcarboxylic acid (94.2 mg.; m.p. 211°-213° C. with gas evolution).

Analysis Calcd. for $C_{11}H_{14}O_3N_2S$: C, 51.95; H, 5.55; N, 11.01. Found: C, 51.84; H, 5.64; N, 10.75.

The other esters of Example 25 are also hydrolyzed, by the method of Examples 26–37, to the products of Examples 26–37, as well as, for example:

4-pentylthiazol-2-ylcarbamoylcarboxylic acid;
4-ethyl-5-propylthiazol-2-ylcarbamoylcarboxylic acid;
4,5-di(2-propyl)thiazol-2-ylcarbamoylcarboxylic acid;
6-methyl-4,5,6,-tetrahydrobenzthiazol-2-ylcarbamoylcarboxylic acid; and
6,6-dimethyl-4,5,6,7-tetrahydrobenzthiazol-2-ylcarbamoylcarboxylic acid.

The acids of Examples 26 to 37 are also prepared by hydrogenolysis of the corresponding benzyl esters, by adaptation of the following specific exemplary method. Benzyl 6,6-dimethyl-4,5,6,7-tetrahydrobenzthiazol-2-ylcarbamoylcarboxylate (1 g.) in 25 ml. of 50:50 water-:ethanol in the presence of 5% palladium on carbon (300 mg.) is hydrogenated at atmospheric pressure and room temperature until uptake of hydrogen is complete (in small excess of one equivalent to account for reduction of the catalyst). The catalyst is removed by filtration and the filtrate evaporated to dryness to yield 6,6-dimethyl-4,5,6,7-tetrahydrobenzthiazol-2-ylcarbamoylcarboxylic acid.

EXAMPLE 38

2-(2-Diethylaminoethylcarbamoylcarboxamido)-thiazole

Ethyl thiazol-2-ylcarbamoylcarboxylate (3.0 g., 15 mmoles) was slurried in 25 ml. of toluene and 2-diethylaminoethylamine (1.8 g., 16 mmoles) added. The mixture was heated to reflux and the resulting solution refluxed for 0.5 hour, at which time tlc indicated reaction was complete. The reaction mixture was cooled and diluted with hexane to precipitate crude product (4.5 g.). Recrystallization from about 60 ml. of isopropyl alcohol gave purified 2-(2-diethylaminoethylcarbamoylcarboxamido)thiazole (3.0 g., m.p. 126°-127° C.).

Analysis Calcd. for $C_{11}H_{18}O_2N_4S$: C, 48.87; H, 6.71; N, 20.72. Found: C, 48,62; H, 6.66; N, 20.70.

EXAMPLE 39

2-[2-(4-Morpholinyl)ethylcarbamoylcarboxamido]-thiazole

Ethyl thiazol-2-ylcarbamoylcarboxylate (3.0 g., 15 mmoles) and 4-(2-aminoethyl)morpholine (2.1 g., 16 mmoles) in 25 ml. of toluene was reacted and crude product (3.7 g.) isolated as detailed in the preceding Example. Recrystallization from approximately 100 ml. of toluene gave purified 2-[2-(4-morpholinyl)ethylcarbamoylcarboxamido]thiazole (2.8 g.; m.p. 187.5°-188.5° C.).

Analysis Calcd. for $C_{11}H_{16}O_3N_4S$: C, 46.46; H, 5.67; N, 19.70. Found: C, 46.65; H, 5.54; N, 19.53.

EXAMPLE 40

2-(3-Diethylaminopropylcarbamoylcarboxamido)-thiazole

Ethyl thiazol-2-ylcarbamoylcarboxylate (2.0 g., 10 mmoles) and 3-diethylaminopropylamine (1.4 g., 11 mmoles) in 25 ml. of toluene were refluxed for 1 hour. The reaction mixture was cooled and crude product (2.25 g.) precipitated by the addition of 75 ml. of hexane. Recrystallization from 65-70 ml. of cyclohexane produced purified 2-(3-diethylaminopropylcarbamoylcarboxamido)thiazole (1.8 g., m.p. 99°-100° C.).

Analysis Calcd. for $C_{12}H_{20}O_2N_4S$: C, 50.68; H, 7.09; N, 19.70. Found: C, 50.52; H, 6.82; N, 19.68.

EXAMPLE 41

2-(2-Diethylaminoethylcarbamoylcarboxamido)cyclopentenothiazole

Ethyl cyclopentenothiazol-2-ylcarbamoylcarboxylate (1.2 g., 5.0 mmoles) and 2-diethylaminoethylamine (639 mg., 5.5 mmoles) were combined and heated to reflux in 15 ml. of toluene for 30 minutes, at which time tlc (chloroform—1% ethanol) indicated reaction was complete. Crude product (1.08 g.) was precipitated by cooling and dilution with hexane. Recrystallization from about 50 ml. of isopropyl ether afforded purified 2-(2-diethylaminoethylcarbamoylcarboxamido)cyclopentenothiazole (815 mg., m.p. 122°-123° C.).

Analysis Calcd. for $C_{14}H_{22}O_2N_4S$: C, 54.16; H, 7.14; N, 18.05. Found: C, 54.34; H, 7.04; N, 18.04.

EXAMPLE 42

2-[2-(4-Morpholinyl(ethylcarbamoylcarboxamido]cyclopentenothiazole

Ethyl cyclopentenothiazol-2-ylcarbamoylcarboxylate (1.2 g., 5 mmoles) and 4-(2-aminoethyl)morpholine (716 mg., 5.5 mmoles) in 15 ml. of toluene were reacted and crude product (1.4 g.) isolated according to the procedures detailed in the preceding Example. Recrystallization from approximately 60 ml. of isopropyl alcohol and then from approximately 50 ml. of absolute ethanol afforded purified 2-[2-(4-morpholinyl)ethylcarbamoylcarboxamido]cyclopentenothiazole (0.92 g.; m.p. 170°-171.5° C.).

Analysis Calcd. for $C_{14}H_{20}O_3N_4S$: C, 51.83; H, 6.21; N, 17.27. Found: C, 51.93; H, 6.46; N, 17.19.

EXAMPLE 43

2-(2-Diethylaminoethylcarbamoylcarboxamido)-4,5,6,7-tetrahydrobenzthiazole

Ethyl 4,5,6,7-tetrahydrobenzthiazol-2-ylcarbamoylcarboxylate (1.3 g., 5 mmoles) and 2-diethylaminoethylamine (0.64 g., 5.5 mmoles) in 15 ml. of toluene were reacted according to the two previous Examples. The reaction mixture was cooled and evaporated to dryness in vacuo. The residue was recrystallized from about 50 ml. of isopropyl ether, affording purified 2-(2-diethylaminoethylcarbamoylcarboxamido)-4,5,6,7-tetrahydrobenzthiazole (900 mg.; m.p. 108.5°-109.5° C.).

Analysis Calcd. for $C_{15}H_{24}O_2N_4S$: C, 55.53; H, 7.46; N, 17.27. Found: C, 55.37; H, 7.67; N, 17.31.

EXAMPLE 44

2-[2-(4-Morpholinyl)ethylcarbamoylcarboxamido]-4,5,6,7-tetrahydrobenzthiazole

Ethyl 4,5,6,7-tetrahydrobenzthiazol-2-ylcarbamoylcarboxylate (1.3 g., 5 mmole) and 4-(2-aminoethyl)morpholine (716 mg., 5.5 mmoles) in 15 ml. toluene were reacted and crude product (1.5 g.) isolated by the procedures detailed in Example 41. Recrystallization from approximately 75 ml. of cyclohexane gave purified 2-[2-(4-morpholinyl)ethylcarbamoylcarboxamido]-4,5,6,7-tetrahydrobenzthiazole (1.2 g.; m.p. 128.5°–130° C.).

Analysis Calcd. for $C_{15}H_{22}O_3N_4S$: C, 53.23; H, 6.55; N, 16.56. Found: C, 53.70; H, 6.82; N, 16.43.

EXAMPLE 45

2-(2-Diethylaminoethylcarbamoylcarboxamido)cycloheptenothiazole

By the procedures detailed in Example 41, ethyl cycloheptenothiazol-2-ylcarbamoylcarboxylate (1.3 g., 5 mmoles) and 2-diethylaminoethylamine (639 mg., 5.5 mmoles) in 15 ml. toluene were reacted and crude product (955 mg.) isolated. Recrystallization from about 40 ml. of hexane produced purified 2-(2-diethylaminoethylcarbamoylcarboxamido)cycloheptenothiazole (720 mg.; m.p. 114.5°–115.5° C.).

Analysis Calcd. for $C_{16}H_{26}O_2N_4S$: C, 56.77; H, 7.74; N, 16.55. Found: C, 56.33; H, 7.86; N, 16.47.

EXAMPLE 46

2-[2-(4Morpholinyl)ethylcarbamoylcarboxamido]cycloheptenothiazole

By the procedures detailed in Example 41, ethyl cycloheptenothiazol-2-ylcarbamoylcarboxylate (1.3 g., 5 mmoles) and 4-(2-aminoethylmorpholine (716 mg., 5.5 mmoles) in 15 ml. of toluene were reacted and crude product (1.4 g.) isolated. Recrystallization from absolute ethanol afforded 2-[2-(4-morpholinyl)ethylcarbamoylcarboxamido]cycloheptenothiazole (885 mg., m.p. 158°–159° C.).

Analysis Calcd. for $C_{16}H_{24}O_3N_4S$: C, 54.52; H, 6.86; N, 15.90. Found: C, 54.54; H, 7.01; N, 16.10.

By the method of Examples 38–46, substituting 2-dimethylaminoethylamine, 2-di(2-propyl)aminoethylamine, 1-(2-aminoethyl)pyrrolidine, 1-(2-aminoethyl)piperidine for 2-diethylaminoethylamine or 4-(2-aminoethyl)morpholine, the corresponding 2-(2-dimethylaminoethylcarbamoylcarboxamido)thiazoles and 2-[di(2-propyl)aminoethylcarbamoylcarboxamido[thiazoles, 2-[2-(1-pyrrolidino)ethylcarbamoylcarboxamido]thiazoles and 2-[2-(1-piperidino)ethylcarbamoylcarboxamido]thiazoles are prepared.

By the same method the other esters of Examples 14–25 are reacted with the appropriate amine to yield the corresponding amides, e.g.:

2-(2-diethylaminoethylcarbamoylcarboxamido)-4-methylthiazole;

2-[2-(4-morpholinyl)ethylcarbamoylcarboxamido]-4,5-dimethylthiazole;

2-[2-dimethylaminoethylcarbamoylcarboxamido)-5-ethylthiazole];

2-[2-di(2-propyl)aminoethylcarbamoylcarboxamido]-4,5-diethylthiazole;

2-[2-(1-piperidinyl)ethylcarbamoylcarboxamido]-4,5,6,7-tetrahydrobenzthiazole; and 2-[2-(1-pyrrolidinyl)ethylcarbamoylcarboxamido]-4,5,6,7-tetrahydrobenzthiazole.

EXAMPLE 47

Sodium 4,5-Diethylthiazol-2-ylcarbamoylcarboxylate 4,5-Diethylthiazol-2-ylcarbamoylcarboxylic acid is combined with an equivalent of sodium ethoxide in ethyl acetate. The sodium salt is isolated by concentration to dryness or by precipitation resulting from addition of a non-solvent (e.g., hexane).

Substitution of an equivalent amount of diethanol amine for sodium ethoxide is employed to produce the corresponding diethanolammonium salt.

EXAMPLE 48

Potassium 4,5,6,7-Tetrahydrobenzthiazol-2-ylcarbamoylcarboxylate 4,5,6,7-Tetrahydrobenzthiazol-2-ylcarbamoylcarboxylic acid is dissolved in ethyl acetate. An equivalent of ethanolic potassium hydroxide is added. The corresponding potassium salt is isolated by concentration to dryness or by precipitation resulting from addition of a non-solvent (e.g., ether or heptane).

Substitution of an equivalent of N-methylglucamine (meglumine) for the ethanolic potassium hydroxide is employed to produce the corresponding N-methylglucammonium salt.

EXAMPLE 49

Sodium 4-Methylthiazol-2-ylcarbamoylcarboxylate

4-Methylthiazol-2-ylcarbamoylcarboxylic acid is dissolved by warming in acetone. An equivalent of sodium methoxide is added with stirring. The corresponding sodium salt is isolated by evaporation to dryness or by precipitation resulting from addition of a non-solvent (e.g., pentane).

Substitution of a molar equivalent of piperazine for sodium methoxide is employed to produce the corresponding piperazinium salt.

EXAMPLE 50

Magnesium 4,5-Dimethylthiazol-2-ylcarbamoylcarboxylate 4,5-Dimethylthiazole-2-ylcarbamoylcarboxylic acid and an equivalent quantity of magnesium oleate are each dissolved in ethanol and the solutions mixed. The corresponding magnesium salt is isolated by concentration and/or addition of heptane.

Substitution of an equivalent of calcium palmitate for magensium oleate in this process is employed to produce calcium 4,5-dimethylthiazol-2-ylcarbamoylcarboxylate.

EXAMPLE 51

Cationic Salt Formation

Alternatively, the acid products of Examples 20 to 37 are converted to the sodium, potassium, ammonium, calcium, magnesium, aluminum, triethylamine, tri-n-butylamine, piperidine, triethanolamine, diethylaminoethylamine, pyrrolidine and N,N-dibenzylethylenediamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE 52

Anionic Salt Formation

Anionic salts (acid addition salts) of the amines of Examples 38 to 46 are prepared by dissolving the amine in ethanol. An equimolar amount of the desired acid (e.g., hydrogen chloride, hydrogen bromide, phosphoric acid, nitric acid, sulfuric acid, benzenesulfonic acid, citric acid, laurylsulfonic acid, fumaric acid, oxalic acid, maleic acid, methanesulfonic acid, tartaric acid, p-toluenesulfonic acid, succinic acid) is dissolved in a separate quantity of ethanol. The two solutions are combined and the salt precipitated by concentration or by the addition of ether, hexane, or other non-solvent.

EXAMPLE 53

Capsules

A blend is prepared containing the following ingredients in the proportion by weight indicated:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient active ingredient to fill standard size capsules so that each contains 250 mg., 100 mg., 50 mg., 25 mg. or 10 mg. of the active ingredient (weight equivalent to free acid or free base when a salt is used). The portion of blend to active drug is within the limits of 1-0.05 to 1-2, i.e., 10 mg. of active ingredient and 200 mg. of blend in a 10 mg. capsule or 250 mg. of active ingredient and 125 mg. of blend in a 250 mg. capsule as exemplary of the extremes.

In like manner, capsules containing 2.0 mg. and 6.0 mg. of active ingredient, and having about 300 mg. of the following blends per capsule are prepared:

| Ingredients | Weight mg./capsule |
|---|---|
| Drug | 2.00 |
| N-methylglucamine | 18.00 |
| Lactose, anhydrous | 251.20 |
| Corn starch, anhydrous | 8.80 |
| Drug | 6.00 |
| N-methylglucamine | 18.00 |
| Lactose, anhydrous | 237.20 |
| Corn starch, anhydrous | 30.00 |
| Talc | 8.80 |

EXAMPLE 54

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this tablet base there is blended sufficient active ingredient to form tablets containing 50 mg., 100 mg., or 250 mg. of active ingredient, as free acid or free base, if a salt is used. The portion of blend to active drug is within the limits of 1-0.167 to 1-1, i.e., 50 mg. of active ingredient and 300 mg. of blend in a 50 mg. tablet or 250 mg. of active ingredient and 250 mg. of blend in a 250 mg. tablet.

EXAMPLE 55

Injectable Preparation

A suspension/solution for parenteral, especially intramuscular injection is prepared with the following composition:

| | |
|---|---|
| Active ingredient | 6.04 g.* |
| Magnesium chloride hexahydrate | 12.36 g. |
| Monoethanolamine | 8.85 g. |
| Propylene glycol | 376.00 g. |
| Water, distilled | 94.00 g. |

*If a salt is employed, actual weight employed is equivalent to this weight of free acid or free base.

The resulting suspension/solution has a concentration of effective ingredient of 10 mg./ml.

EXAMPLE 56

Injectable Preparation

Sterile active ingredient is dry filled into vials such that each vial contains 55 mg. of the active ingredient. Immediately before use, 11 ml. of sterile water for injection is added to give a 5 mg./ml. suspension/solution suitable for parenteral injection. Those dosage forms which are solutions by this method are generally suitable for intravenous, intramuscular or subcutaneous injection, while suspensions are suitable primarily for intramuscular injection.

I claim:

1. A compound of the formula $$\begin{array}{c} R' \\ \diagup \\ R'' \end{array} \!\!\! \begin{array}{c} S \\ \diagdown \\ N \end{array} \!\!\! \begin{array}{c} \\ \diagup \\ \diagdown \end{array} \!\!\! \begin{array}{c} O \\ \| \\ N \\ | \\ H \end{array} \!\!\! \begin{array}{c} \\ \diagdown \\ \diagup \end{array} \!\!\! \begin{array}{c} \\ \| \\ O \end{array} \!\!\! X$$

wherein
X is hydroxy, $(C_1-C_5)$-alkoxy, phenoxy, benzyloxy, or $-NH(CH_2)_nY$ wherein n is an integer of value 2 to 4 and Y is di-$(C_1-C_3)$-alkylamino, 1-pyrrolidinyl, 1-piperidinyl or 4-morpholinyl;
R' and R'' when taken together are $(C_3-C_8)$-alkylene, with the proviso that the ring so formed is 5- to 8-membered;
R' and R'' when taken separately are each independently hydrogen, $(C_1-C_6)$-alkyl or $(C_5-C_6)$-cycloalkyl, with the proviso that when X is other than $-NH(CH_2)_nY$, at least one of R' and R'' is other than hydrogen;
the pharmaceutically acceptable cationic salts thereof when X is hydroxyl, and the pharmaceutically acceptable anionic salts thereof when X is $-NH(CH_2)_nY$.

2. A compound of claim 1 wherein X is $(C_1-C_3)$-alkoxy, phenoxy, benzyloxy, or $-NH(CH_2)_2Y$.

3. A compound of claim 2 wherein X is $(C_1-C_3)$-alkoxy.

4. A compound of claim 3 wherein X is ethoxy.

5. A compound of claim 4 wherein R' and R'' are taken together.

6. The compound of claim 5 wherein R' and R'' are butylene.

7. A compound of claim 4 wherein R' and R" are taken separately and are each hydrogen or $(C_1-C_3)$-alkyl.

8. A compound of claim 7 wherein R' is hydrogen.

9. The compound of claim 8 wherein R" is methyl.

10. The compound of claim 8 wherein R" is ethyl.

11. A compound of claim 7 wherein R" is hydrogen.

12. The compound of claim 11 wherein R' is methyl.

13. The compound of claim 11 wherein R' is ethyl.

14. A compound of claim 7 wherein R' and R" are each $(C_1-C_3)$-alkyl.

15. The compound of claim 14 wherein R' and R" are each methyl.

16. The compound of claim 14 wherein R' is methyl and R" is ethyl.

17. The compound of claim 14 wherein R' is ethyl and R" is methyl.

18. The compound of claim 14 wherein R' and R" are each ethyl.

19. A compound of claim 2 wherein X is $-NH(CH_2)_2Y$.

20. A compound of claim 19 wherein R' and R" are taken together and are butylene.

21. The compound of claim 20 wherein Y is diethylamino.

22. The compound of claim 20 wherein Y is 4-morpholinyl.

* * * * *